(12) United States Patent
Pfirrmann

(10) Patent No.: US 9,241,943 B2
(45) Date of Patent: Jan. 26, 2016

(54) OXATHIAZINE DERIVATIVES AS ANTIBACTERIAL AND ANTICANCER AGENTS

(71) Applicant: GEISTLICH PHARMA AG, Wolhusen (CH)

(72) Inventor: Rolf W. Pfirrmann, Weggis (CH)

(73) Assignee: Geistlich Pharma AG, Wolhusen (CH)

( * ) Notice: Subject to any disclaimer, the term of this patent is extended or adjusted under 35 U.S.C. 154(b) by 0 days.

(21) Appl. No.: 14/409,352

(22) PCT Filed: Jun. 17, 2013

(86) PCT No.: PCT/IB2013/001261
§ 371 (c)(1),
(2) Date: Dec. 18, 2014

(87) PCT Pub. No.: WO2013/190355
PCT Pub. Date: Dec. 27, 2013

(65) Prior Publication Data
US 2015/0182534 A1    Jul. 2, 2015

Related U.S. Application Data

(60) Provisional application No. 61/661,092, filed on Jun. 18, 2012, provisional application No. 61/694,452, filed on Aug. 29, 2012.

(51) Int. Cl.
*C07D 291/06* (2006.01)
*A61K 31/54* (2006.01)
*C07D 327/10* (2006.01)
*A61K 31/39* (2006.01)
*A61K 45/06* (2006.01)

(52) U.S. Cl.
CPC .................. *A61K 31/54* (2013.01); *A61K 31/39* (2013.01); *A61K 45/06* (2013.01); *C07D 291/06* (2013.01); *C07D 327/10* (2013.01)

(58) Field of Classification Search
CPC ...................................................... C07D 291/06
USPC ............................................ 544/2; 514/222.5
See application file for complete search history.

(56) References Cited

U.S. PATENT DOCUMENTS 3,202,657 A * 8/1965 Kuhne et al. ...................... 544/2
3,394,109 A   7/1968 von der Emden et al.

FOREIGN PATENT DOCUMENTS

WO    00/15232 A1    3/2000
WO    01/39763 A2    6/2001

OTHER PUBLICATIONS

F. Borcard et al.: "Synthesis of new oxathiazinane dioxides and their in vitro cancer cell growth inhibitory activity," Bioorganic and Medicinal Chemistry Letters, vol. 20, Sep. 2009, pp. 5353-5356.

* cited by examiner

*Primary Examiner* — Kahsay Habte
(74) *Attorney, Agent, or Firm* — Rothwell, Figg, Ernst & Manbeck, P.C.

(57) ABSTRACT

New oxathiazin-like compounds and their derivatives are useful as antineoplastic and antimicrobial agents.

15 Claims, 5 Drawing Sheets

OXATHIAZINE DERIVATIVES AS ANTIBACTERIAL AND ANTICANCER AGENTS

CROSS-REFERENCE TO RELATED APPLICATIONS

This application is a 35 U.S.C. §371 National Phase Entry Application from PCT/IB2013/001261, filed Jun. 17, 2013, and designating the United States, and claims the benefit of U.S. Provisional Patent Application No. 61/661,092 filed on Jun. 18, 2012, and of U.S. Provisional Patent Application No. 61/694,452 filed on Aug. 29, 2012, which are incorporated herein by reference in their entireties.

BACKGROUND OF THE INVENTION

1. Field of the Invention

The present invention relates to new compounds and uses thereof.

2. Description of the Background Art

Many compounds are known, e.g., for treatment of cancers in patients or for treatment of microbial infections in patients.

There remains a need in the art for new compounds with more potent antineoplastic and antimicrobial activity, less toxicity and side effects, and less resistance to treatment by tumor or microbial cells.

SUMMARY OF THE INVENTION

In accordance with the present invention, new oxathiazin-like compounds and their uses are disclosed.

DETAILED DESCRIPTION OF THE INVENTION

Figure 1:
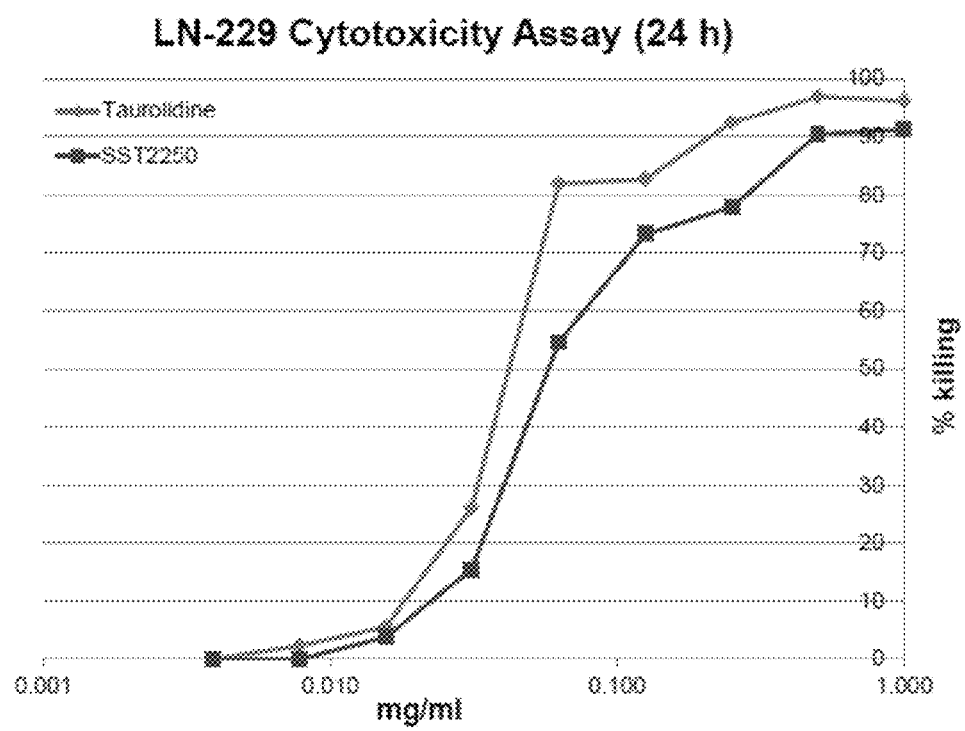
FIG. 1 graphically shows anti-neoplastic activity of one embodiment of the invention in a cytotoxicity assay in LN-229 cells.

According to certain embodiments, the present invention relates to oxathiazin-like compounds, as well as derivatives thereof.

Oxathiazin-like compounds and derivatives thereof according to certain embodiments of the present invention have antineoplastic activities, antimicrobial activities and/or other activities.

In certain embodiments, compounds of the present invention are useful, inter alia, in the treatment of cancers and tumors in a subject, such as a human patient. Accordingly, in certain embodiments the present invention also relates to treatment of cancers and tumors using compounds described herein. Cancers such as central nervous system cancers including glioblastoma, glioma, neuroblastoma, astrocytoma, and carcinomatous meningitis, colon cancer, rectal cancer and colo-rectal cancer, ovarian cancer, breast cancer, prostate cancer, lung cancer, mesothelioma, melanoma, renal cancer, liver cancer, pancreatic cancer, gastric cancer, esophageal cancer, urinary bladder cancer, cervical cancer, cardiac cancer, gall bladder cancer, skin cancer, bone cancer, cancers of the head and neck, leukemia, lymphoma, lymphosarcoma, adenocarcinoma, fibrosarcoma, and metastases thereof, for example, are diseases contemplated for treatment according to certain embodiments of the invention. Drug resistant tumors, for example a multiple drug resistant (MDR) tumor, also are useful in certain embodiments using the inventive compounds, including drug resistant tumors which are solid tumors, non-solid tumors and lymphomas. It is presently believed that any neoplastic cell can be treated using the methods described herein.

Tumor stem cells (also referred to as cancer stem cells (CSCs)) are considered to be the main drivers for the formation of metastases and the regrowth of tumors after resection.

In certain embodiments, compounds of the present invention are useful, inter alia, in the treatment of tumor stem cells in a subject.

In certain embodiments, compounds of the present invention are useful, inter alia, in the treatment of glioblastoma tumor stem cells in a subject.

In certain embodiments, the invention kills tumor cells and/or CSCs, or inhibits their growth, by oxidative stress, apoptosis and/or inhibiting growth of new blood vessels at the tumor site (anti-angiogenesis and anti-tubulogenesis). A primary mechanism of action for killing tumor cells and/or CSCs is oxidative stress. Tumor cells and/or CSCs may also be killed by apoptosis according to the invention. At lower blood concentrations, compounds according to the invention are effective at inhibiting tumor cell growth by their anti-angiogenic action and their anti-tubulogenic action, and these compounds are thus useful for palliative treatment.

Oxathiazin-like compounds and derivatives thereof of the invention metabolize much slower in the bloodstream than taurolidine and taurultam. Accordingly, lower doses of such compounds can be administered to a patient to achieve similar effects.

Compounds of the present invention also are useful, in certain embodiments, in treatment of microbial infections in a subject, such as a human patient. Microbial infections which may be treated according certain embodiments include bacterial infections, fungal infections and/or viral infections.

Cancer patients tend to be immunocompromised, making them particularly susceptible to microbial infections, especially during and/or after surgery.

In certain embodiments, compounds of the invention are utilized to treat glioblastoma in a subject.

In certain embodiments, compounds of the invention are utilized to treat *S. aureus* infection in a subject.

In certain embodiments, compounds of the invention are utilized according to the invention to treat MRSA in a subject.

In certain embodiments, compounds of the invention are utilized according to the invention to treat *E. coli* in a subject.

In certain embodiments, compounds of the invention are utilized according to the invention to treat *H. pylori* in a subject, and/or cancer(s) associated with *H. pylori* in a subject.

In certain embodiments, compounds of the invention are utilized according to the invention to treat HIV in a subject.

In certain embodiments, compounds according to formula I are utilized according to the invention wherein R is H, alkyl, or the like, such as methyl, ethyl, propyl, (e.g., isopropyl), benzyl or the like.

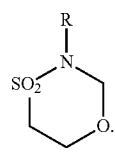

Formula I

In certain embodiments, new compound 2250 (Tetrahydro1,4,5-oxathiazin-4-dioxid) is utilized according to the invention.

In certain embodiments, new compound 2245 is utilized according to the invention.

Compound 2250 prevents and treats stomach tumors, including tumors caused by or associated with *H. pylori*.

The amount of the compounds needed depends on tumor size. In one embodiment, the invention includes surgically reducing tumor size and treating with one or more of the compounds. The compound may be administered before, during or after surgery to reduce tumors. Compounds according to the invention can be administered by any suitable method, including without limitation, by capsules, tablets, IV,IP and/or directly to the tumor.

It was unexpectedly found that the compounds could be administered during surgery and immediately after surgery because the compounds do not inhibit wound healing like other chemotherapy agents.

It was unexpectedly found that taurolidine, taurultam, and Oxathiazin-like compounds and derivatives thereof kill tumor stem cells, which is very unusual and perhaps unknown among chemotherapy agents. Typical chemotherapy agents, if effective against tumor stem cells, generally are only effective at very high doses which are extremely toxic to human patients.

It was unexpectedly found that lower doses of taurolidine and/or taurultam killed tumor stem cells than were needed to kill tumor cells.

It was unexpectedly found that Oxathiazin-like compounds and derivatives thereof have a half-life in human blood that is significantly longer than the half-life of taurolidine and taurultam. Accordingly, these compounds are cleared less rapidly from the bloodstream of the patients, thereby effectively delaying loss of drug potency caused by the body's clearance mechanisms.

Thus, the half-life of compound 2250 is greater than 24 hours in human blood, which is significantly higher than the half-life of taurolidine, which was found to be ~30 minutes using the same test.

In some embodiments, the compounds are administered in compositions at a concentration of about 0.01 to about 1000 µg/ml. In some embodiments, the compounds are administered in compositions at a concentration of about 1 to about 100 µg/ml. In some embodiments, the compounds are administered in compositions at a concentration of about 10 to about 50 µg/ml. The composition may also contain about 0.01 to about 1000 µg/ml, about 1 to about 100 µg/ml, or about 10 to about 50 µg/ml taurolidine and/or taurultam.

In some embodiments, the compounds are administered in compositions at a concentration of about 0.01 to about 3%. In some embodiments, the compounds are administered in compositions at a concentration of about 0.1 to about 2.5%. In some embodiments, the compounds are administered in compositions at a concentration of about 1% to about 2%. The composition may additionally contain about 0.01 to about 3%, about 0.1 to about 2.5%, or about 1 to about 2% taurolidine and/or taurultam.

In one embodiment, the Oxathiazin-like compounds and derivatives thereof may be administered as a co-therapy with taurolidine and/or taurultam to kill tumor stem cells. In accordance with such an embodiment, the co-therapy has been unexpectedly found to require a lower dosage of drug to kill tumor stem cells than necessary to kill normal tumor cells.

In one embodiment, the compound is administered to the subject at a total daily dose of from about 0.1 g to about 100 g, about 1 g to about 80 g, about 2 g to about 50 g, or about 5 g to about 30 g.

Effective dosage amounts of the compounds are dosage units within the range of about 0.1-1,000 mg/kg, preferably 150-450 mg/kg per day, and most preferably 300-450 mg/kg per day.

Suitable formulations for injection or infusion may comprise an isotonic solution containing one or more solubilizing agents, e.g., polyols such as glucose, in order to provide solutions of increased compound concentration. Such solutions are described in EP 25366261. The solution can be rendered isotonic with ringer solution or ringer lactate solution. The concentration of the compound in such solutions may be in the range 1-60 g/liter. Exemplary compounds of the invention include the following:

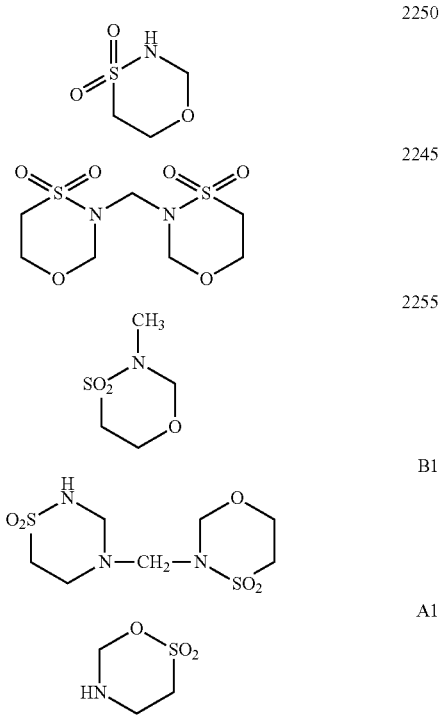

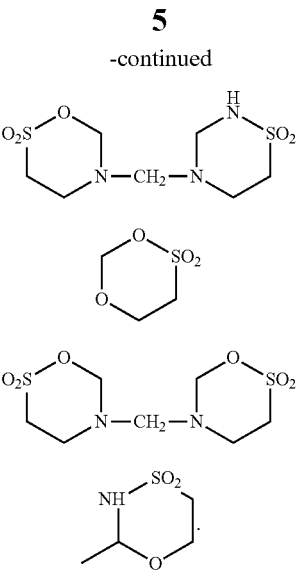

In certain embodiments, the invention also relates to derivatives of the above compounds having, e.g., activity as described herein of said compounds, for example, at least 25%, 30%, 40%, 50%, 60%, 70%, 80%, 90%, 95%, 100%, or more, of said activity.

In certain embodiments, the invention also relates to compositions containing the compounds described herein, including pharmaceutically acceptable solutions of said compounds, as well as orally administrable compositions such as capsules and tablets containing said compositions.

In certain embodiments, the compounds of the present invention can be administered to a subject or patient by any suitable means, for example, in solution, e.g., locally, systemically such as by intravenous infusion, or the like.

Synthesis of 2250

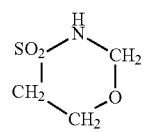

sublimes in a vacuum at ~70-80° C.
Starting materials:
Isethionic Acid,
Carbylsulfat, Taurin, Taurinamide,
Cysteine, Isethionic Acid, inter alia
Synthesis 1
I.
  a. Isethionic Acid via Carbylsulfate

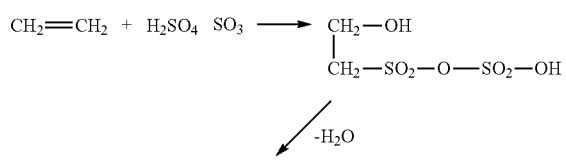

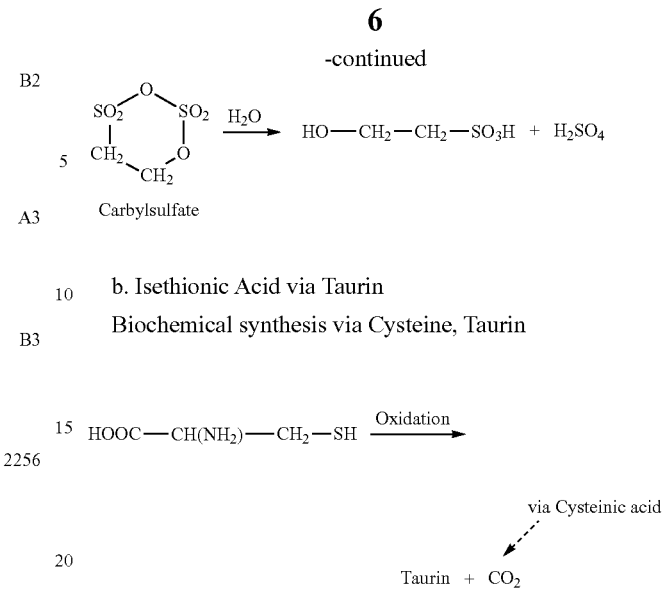

b. Isethionic Acid via Taurin

Biochemical synthesis via Cysteine, Taurin $$HOOC-CH(NH_2)-CH_2-SH \xrightarrow{Oxidation}$$

via Cysteinic acid

Taurin + $CO_2$

Taurin $\xrightarrow{Biotransformation}$ Isethionic Acid

Chemical synthesis ethylenoxide with bisulfite

II. Isethionic Amide $$HO-CH_2-CH_2-SO_2-NH_2$$

a.

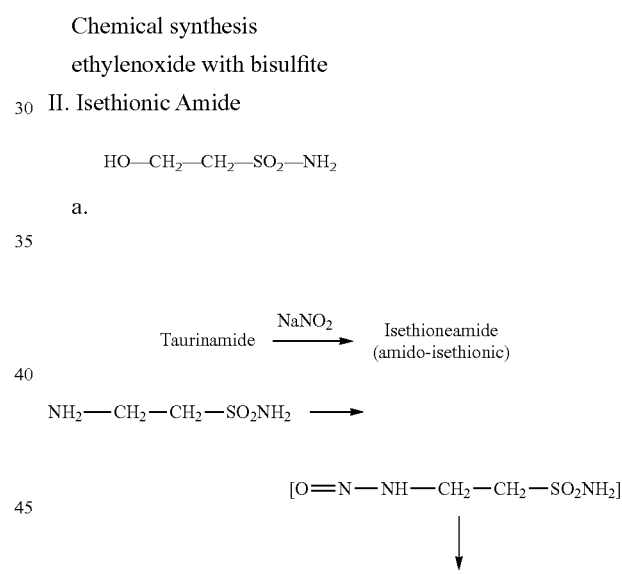

b. Carbylsulfate+$NH_3$

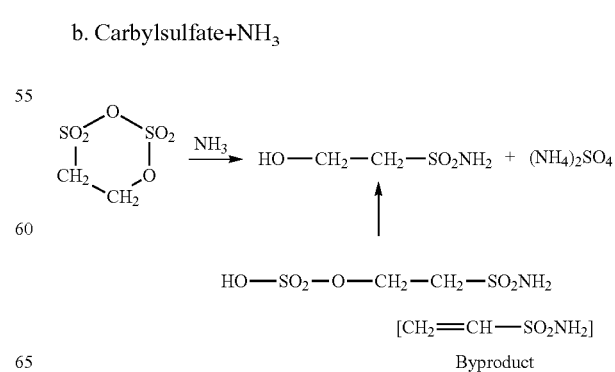

Possible Alternative Chemical Synthesis Steps for 2250
a) Sulfamic acid
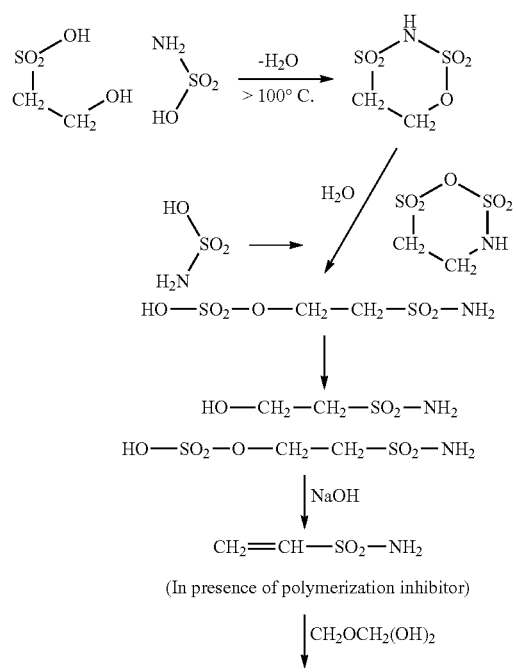
b) Paraformaldehyde, Hexamethylenetetramine (Hexamine, Formine, Urotropin)
c)
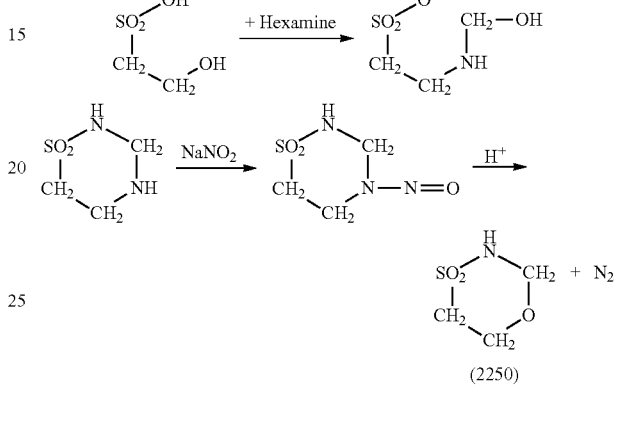
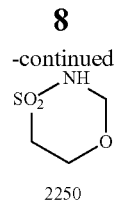
2250
d)
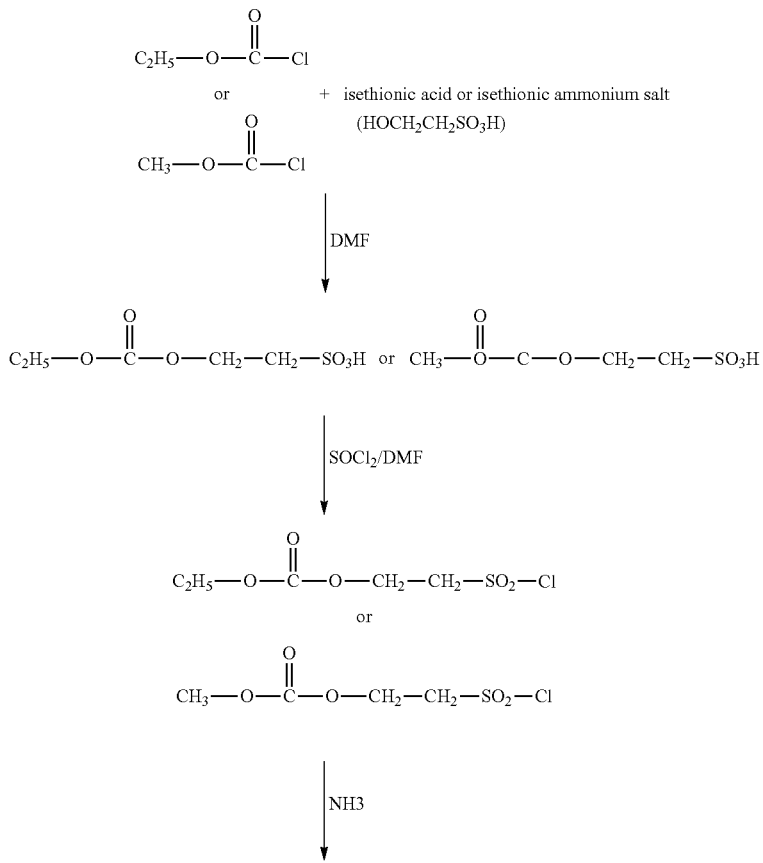

-continued $$C_2H_5-O-\overset{O}{\underset{\|}{C}}-O-CH_2-CH_2-SO_2-NH_2$$

or $$CH_3-O-\overset{O}{\underset{\|}{C}}-O-CH_2-CH_2-SO_2-NH_2$$

Several Alternative Synthesis Steps for 2250 and 2255
I. Starting Materials 2250/2255
  a.

$$\text{Taurinamide} \xrightarrow{\text{NaNO}_2} \text{Isethionicamide} + N_2$$

b.

Carbylsulfate + H$_2$O

Ethionic acid

↓ H$_2$O

Isethionic acid

Synthesis sodiumisethionate from Ethylenoxide+Sodium-hydrogensulfite
II. Reaction of Amine with Carbylsulfate $$R-NH-SO_2-CH_2-CH_2-O-SO_3Na$$

↓ H$_2$C(OH)$_2$

R—N(SO$_2$—CH$_2$—CH$_2$—O—CH$_2$)

[structure: Ph-CH$_2$—N(SO$_2$—CH$_2$—CH$_2$—O—CH$_2$)] $\xrightarrow{H_2/P_t}$ 2250
Toluen/Methylcyclohexane

III.

2250 ⟶ +CH$_2$(OH)$_2$/HCOOH

CH$_3$—N(SO$_2$—CH$_2$—CH$_2$—O—CH$_2$)

(2255)

Synthesis of 2256

$$\overset{NH_3}{\underset{Cl^-}{}}\text{—CH}_2\text{—CH}_2\text{—}\overset{NH_2}{\underset{SO_2}{}} \xrightarrow{NaNO_2}$$

-continued $$HO-CH_2-CH_2-SO_2-NH_2 \xrightarrow{\text{Acetaldehyde}} \underset{2256}{[\text{morpholine-like ring with NH-SO}_2\text{-O and CH}_3]}$$

40 g taurinamide hydrochloride, 18 g Sodium nitrite and 300 ml of distilled water were boiled together under reflux until no more gas was created. The clear yellow solution was then cooled to 50° C.

30 ml of 1N NaOH was added to 10.5 g of acetaldehyde. The clear yellow solution was left over the weekend under vacuum to dry. The result was a rust-red honey-like residue weighing 37.6 g, which was extracted with ethyl alcohol. The alcohol solution was filtered and concentrated on a rotary evaporator to dry. The resulting dense oil residue was dissolved with ethyl acetate. The ethyl acetate solution was filtered, and concentrated.

This resulted in 30.7 g of dense oil, rust-like color. From the dense oil, white crystals were isolated. The melting point is about 114-116° C.

The IR spectrum confirmed that the resulting compound had the structure of compound 2256:

2256

[structure of compound 2256]

In certain embodiments, a sublimation apparatus, comprised of laboratory glassware known in the art, may be used in a technique of sublimation to purify compounds according to the invention. In certain embodiments, a sublimation vessel is heated under vacuum and under reduced pressure. The compound volatizes and condenses as a purified compound on a cooled surface, leaving non-volatile residue impurities behind. This cooled surface often takes the form of a cold finger. After heating ceases and the vacuum is released, the sublimed compound can be collected from the cooled surface.

In one embodiment, this disclosure includes a method of killing tumor stem cells by administering to a subject in need thereof a tumor stem cell killing effective amount of taurolidine, taurultam, or a mixture thereof. The tumor stem cell killing effective amount of taurolidine and/or taurultam is less than an amount of taurolidine and/or taurultam required for killing tumor cells.

In some embodiments, the taurolidine, taurultam, or a mixture thereof is administered in a tumor stem cell killing composition at a concentration of about 0.01 to about 500 µg/ml. In some embodiments, the taurolidine, taurultam, or a mixture thereof is administered in a tumor stem cell killing composition at a concentration of about 0.1 to about 100 µg/ml. In some embodiments, the taurolidine, taurultam, or a mixture thereof is administered in a tumor stem cell killing effective composition at a concentration of about 10 to about 50 µg/ml. Taurolidine is effective at killing tumor stem cells in tissue culture in vitro at 0.01 µg/ml.

In some embodiments, the taurolidine, taurultam, or a mixture thereof is administered in a tumor stem cell killing composition at a concentration of about 0.001 to about 2%. In some embodiments, the taurolidine, taurultam, or a mixture thereof is administered in a tumor stem cell killing composition at a concentration of about 0.01 to about 1.5%. In some embodiments, the taurolidine, taurultam, or a mixture thereof is administered in a tumor stem cell killing composition at a concentration of about 0.1% to about 1%.

In one embodiment, the taurolidine, taurultam, or a mixture thereof is administered for tumor stem cell killing to a subject in need thereof at a total daily dose of from about 0.01 g to about 50 g, about 0.1 g to about 30 g, about 0.5 g to about 10 g, or about 1 g to about 5 g.

Tumor stem cell killing effective dosage amounts of the taurolidine, taurultam, or a mixture thereof are dosage units within the range of about 0.01-500 mg/kg, preferably 1-100 mg/kg per day, and most preferably 5-50 mg/kg per day. In another embodiment, this disclosure includes a method of killing tumor stem cells by administering to a subject in need thereof a compound selected from the following compounds:

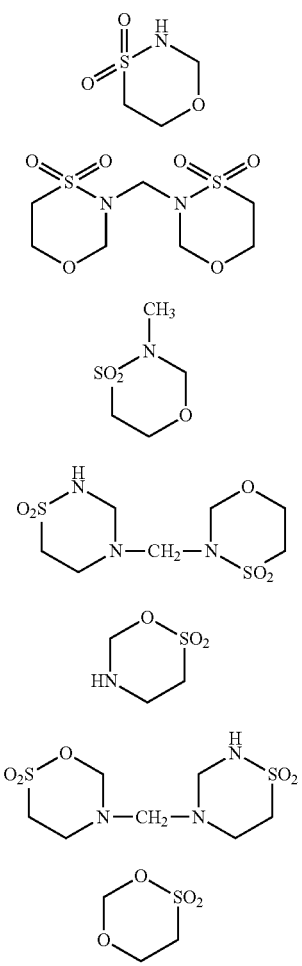

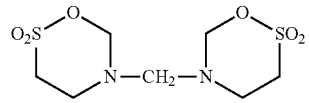

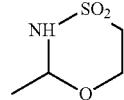

in combination with taurolidine and/or taurultam. Such a technique provides a method for killing tumor stem cells using at least two compounds having different half-lives, and thereby broadening the pharmacokinetic effects obtained thereby.

EXAMPLES

Example 1

Figure 2:
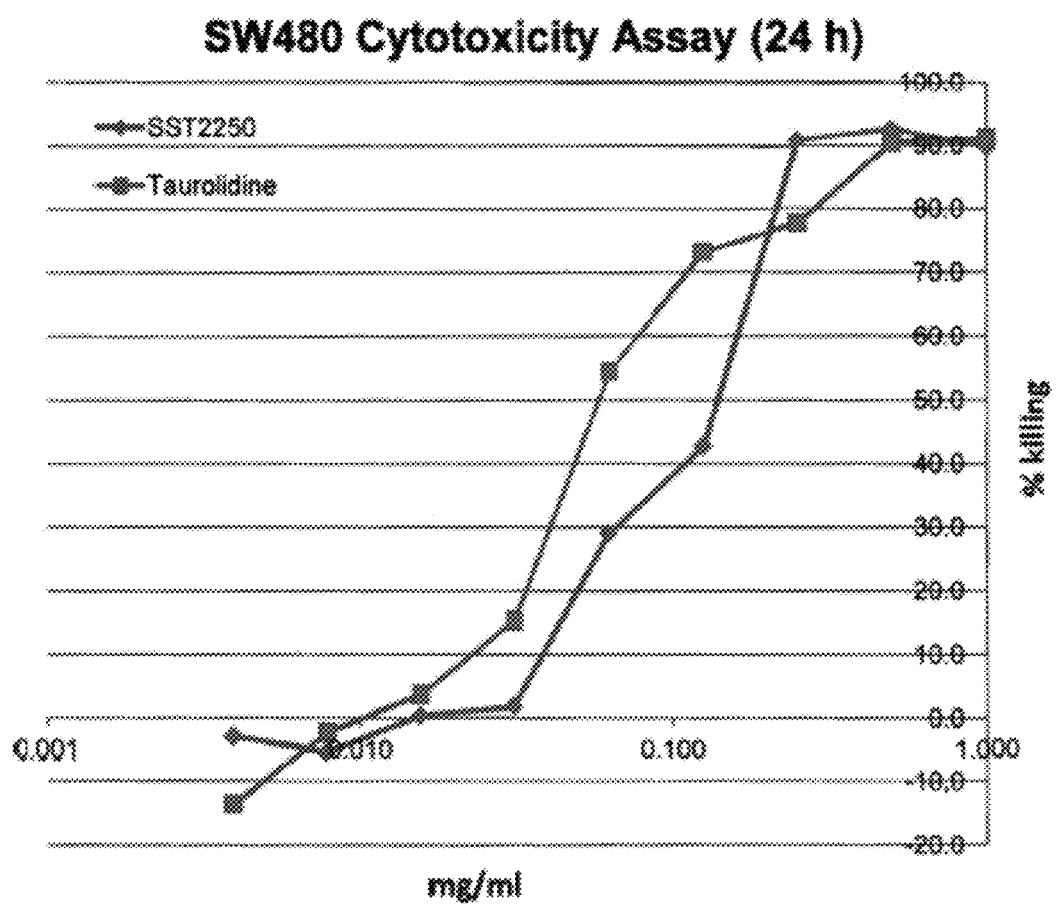
FIG. 2 graphically shows anti-neoplastic activity of one embodiment of the invention in a cytotoxicity assay in SW480 (human colon adenocarcinoma) cells.

Anti-neoplastic activity of compound 2250
Introduction
Based on the recognition of taurolidine as a powerful antineoplastic agent, the analogue 2250 was synthesized by Geistlich Pharma. The present report describes the results from tests of its anti-neoplastic activity in vitro.
Material and Methods
Chemicals: The compound 2250 and taurolidin 2% solution were provided by Geistlich Pharma AG, Wolhusen, assignee of the present invention.
Cell lines: The human glioma cell line LN-229 was used as described previously (Rodak et al. 2005) as well as the human colon adenocarcinoma cell line SW480.
Cytotoxicity assay: Dissociated LN-229 cells were seeded into 96-well plates at a density of $10^4$ cells per well in 100 µl of culture medium. Approximately 24 h later, when the cells had reached 70-80% confluency, the medium was changed and treatment with compound #2250 (4.0-1000 µg/ml), taurolidine (4.0-1000 µg/ml) or standard medium was started. Triplicate cultures were prepared for each sample. After 24 h of incubation at 25° C., the remaining adherent viable cells were stained using crystal violet as described (Rodack et al. 2005). Cell viability was determined by measuring the absorbancy at 540 nm. The results are expressed as killing rate given by the difference between 100% of cells and percentage of cells surviving. $EC_{50}$ values correspond to the concentration inducing 50% cell death.
Results
Positive control: After incubating the human glioblastoma cells (LN-229) for 24 h with taurolidine, a concentration-dependent cytotoxicity was determined (Tab. 1, FIG. 1) with an $EC_{50}$=45 µg/ml, a value which corresponds to earlier results obtained with this cell line (Rodack et al. 2005).
Test of 2250: When 2250 was incubated under the same experimental conditions as taurolidine, a similar concentration-dependent loss of cell viability was observed. The half-maximal concentration of inducing cell death was $EC_{50}$=50 µg/µl (Tab. 1, FIG. 1).
The results for SW480 cell cytotoxicities are shown in FIG. 2.
Discussion
The compound 2250 represents a new avenue in the search for novel antineoplastic agents of the taurolidine-type. Biologically, the compound is as potent as taurolidine. Chemically, the compound shows strikingly different features from taurolidine. By replacing a NH group by an ether-oxygen, the double ring structure of taurolidine is avoided. Compound 2250 is a single ring structure and a close structural analogue of taurultam.

Mechanistically, the results show that the antineoplastic activity of taurolidine is unlikely to be due to the formation of a methoxy-derivative, since 2250 is devoid of a methoxy group. The compound causes blebbing of tumor cells.

Summary

The compound 2250 shows potent antineoplastic activity in vitro, as determined for human glioblastoma cells (cell line LN-229). Its potency ($EC_{50}$=45 µg/ml) is comparable to that of taurolidine ($EC_{50}$=50 µg/ml) as tested in the same cell line.

TABLE 1

Cytotoxicity of 2250 and taurolidine against LL-229 glioblastoma cells.

| Concentration µg/ml | 1000 | 500 | 250 | 125 | 62.5 | 31 | 15.5 | 8 | 4 | — |
|---|---|---|---|---|---|---|---|---|---|---|
| Taurolidine OD ± SD | 0.109 ± 0.010 | 0.098 ± 0.007 | 0.165 ± 0.002 | 0.305 ± 0.008 | 0.317 ± 0.008 | 1.132 ± 0.042 | 1.434 ± 0.031 | 1.478 ± 0.040 | 1.530 ± 0.026 | 1.435 ± 0.009 |
| Comp. 2250 OD ± SD | 0.189 ± 0.007 | 0.141 ± 0.007 | 0.120 ± 0.012 | 0.199 ± 0.014 | 0.372 ± 0.006 | 1.482 ± 0.099 | 1.482 ± 0.029 | 1.527 ± 0.033 | 1.477 ± 0.069 | 1.483 ± 0.013 |

The values were measured in triplicate and the OD is the absorbance at 540 nm plus minus standard deviation (SD). High values correspond to high cell viability.

Example 2

The new compound 2250 (Tetrahydro1,4,5-oxathizain-4-dioxid) was tested and found to have a very high level of antibacterial activity against *Staphylococcus aureus* and *Escherichia coil*. The antibacterial activity against *Staph. aureus* is about double as high as Taurultam.

Example 3

In punch plate tests, Compound 2250 was tested and found highly active against MRSA lines 188, 189, 193, 194 and 195.

Example 4

Each of compounds identified herein as compound 2250, 2255, 2245, A1, A3, B1, B2, or B3 is tested against cancer cell lines of cancers identified herein, and found to be active against such cell lines.

Example 5

Each of compounds identified herein as compound 2250, 2255, 2245, A1, A3, B1, B2, or B3 is administered to patients having cancers identified herein, and found to be effective in treating such cancers.

Example 6

The half-life of compound 2250 in human fresh blood was measured at 37° C. in vitro by GC, PYE Unicam Series 204 FID.
Baseline Value: 49.0 ppm
After 1 hour: 50.6 ppm
After 2 hours: 47.6 ppm
After 20 hours: 38.6-39.0 ppm.

Thus, the half-life of compound 2250 is greater than 24 hours in human blood, which is significantly higher than the half-life of taurolidine, which was found to be —30 minutes using the same test.

Example 7

Tissue samples from high grade gliomas WHO grade IV from newly diagnosed patients (medium age of 54±10 years) were minced mechanically, digested enzymatically and the dissociated cells were filtered. The isolated tumor cells were cultured as bulk cells. Cancer Stem Cells (CSCs) were isolated by the formation of neurospheres under neurosphere conditions (using neurobasal medium) from the murine SMA 560 glioma cell line or from freshly isolated human glioblastoma cells.

Cytotoxicity Assay

Bulk glioma tumor cells were cultured and incubated with taurolidine or taurultam for 24h or 48h as described previously (Rodak et al., J. Neurosurg. 102, 1055-1068, 2005). CSCs were cultured for 7 days and subsequently exposed to taurolidine, taurultam or temozolamide for 24 hours. The number of remaining adherent cells were stained (crystal violet or Alamar Blue) and quantified by absorbance measurements (540 nm). Cell survival was expressed as the percentage of cells surviving relative to the number of cells surviving in untreated control cultures. The results are given as % killing rate or $EC_{50}$ as the dose required for half-maximal cytotoxicity.

Results

Cytotoxicity of Taurolidine and Taurultam Against Cancer Cells and Cancer Stem Cells from the Mouse The mouse SMA560 glioma cell line was used to provide tumor bulk cells and CSCs. Following incubation of SMA560 bulk cells with various concentrations of taurolidine and taurultam (6.25, 12.5, 25, 50, 100, 200 µg/ml), cytotoxicity was determined after 24 h and 48 h of incubation. For both taurolidine and taurultam, a clear dose-dependent cytotoxicity was found with no major difference in potency between the 24 h and 48 h time of incubation (FIG. 3A,B). The $EC_{50}$ value was 34.6 µg/ml for taurolidine and 19.3 µg/ml for taurultam (FIG. 3C).

Figure 5:
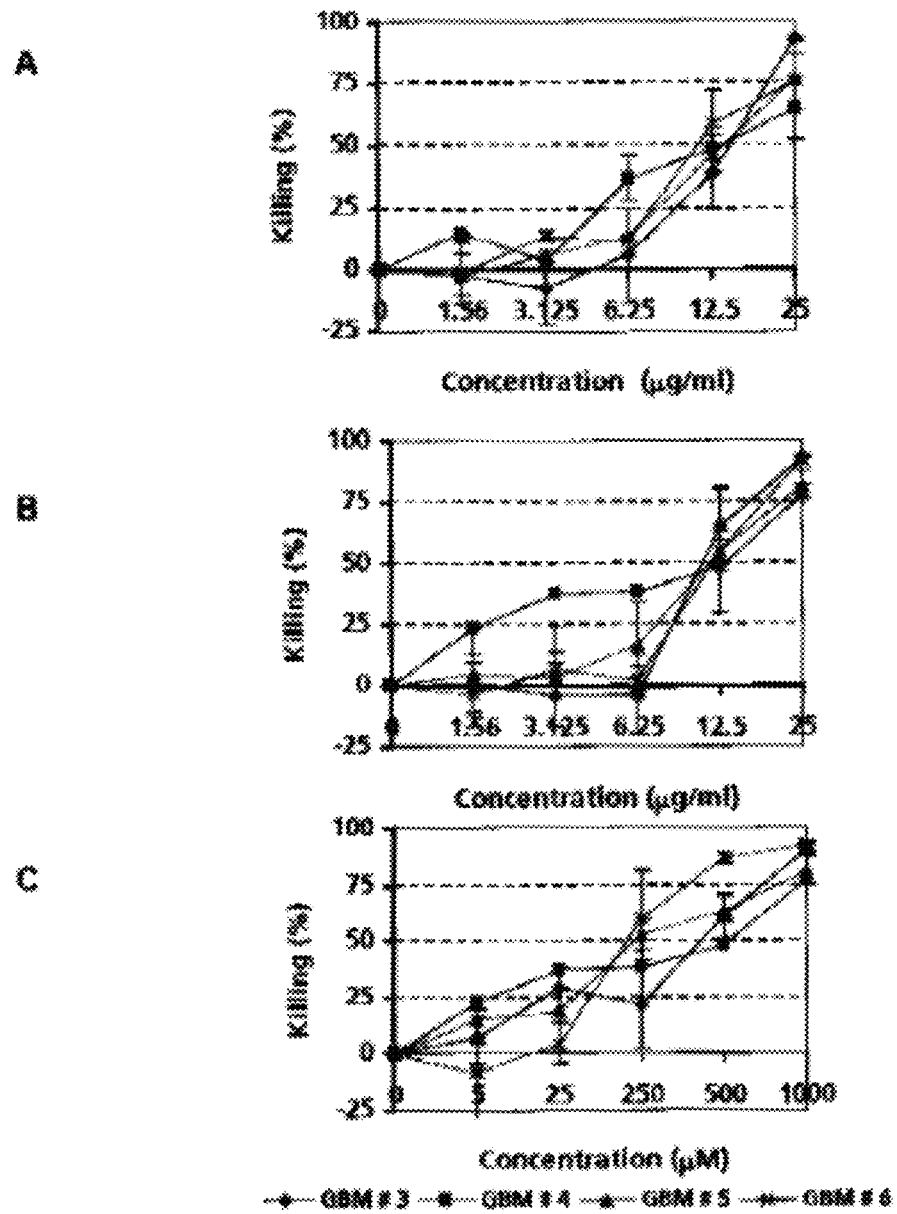
FIG. 5A-C Cytotoxicity induced in cancer stem cells isolated from four glioblastoma multiforme (GBM) patients (GBM #3, #4, #5 and #6) after treatment for 24 h with taurolidine (FIG. 5A), taurultam (TT) (FIG. 5B) or temozolamide (FIG. 5C). Data are presented as mean values±SD.

Mouse CSCs were generated from the SMA560 glioma cell line and cultured for 7 days. The CSCs were treated with the same concentration of taurolidine and taurultam as above and cytotoxicity was determined after 24 hours. As shown in FIG. 5, both taurolidine and taurultam showed a dose dependent cytotoxicity with an $EC_{50}$ of 12.5 µg/ml for taurolidine and $EC_{50}$ of 10 µg/ml for taurultam against murine CSCs. These values demonstrate for the first time that taurolidine and taurultam are effective against a CSC.

Taurolidine and Taurultam Induce Cell Death in Human CSC Isolated from Four Different Glioblastoma Patients.

CSCs were isolated from glioblastoma tissue resected from four patients. The same range of concentrations of taurolidine and taurultam was applied as above and the cytotoxicity was measured after 24 hours of incubation with drug. All four glioblastoma CSCs tested (GBM #3, #4, #5 and #6) were similarly sensitive to taurolidine and taurultam (FIG. 5A,B). The mean $EC_{50}$ value of taurolidine was 13±2 µg/ml, the $EC_{50}$ value of taurultam was 11±1.4 µg/ml (Table 2). In these experiments, the cytotoxic capacity of taurolidine and taurultam was compared with that of temozolamide (TIM) applied in the concentration range of 5 µM to 1,000 µM (FIG. 2C). The mean $EC_{50}$ value of TMZ was 68.5±26 µg/ml (Table 2). Interestingly, this concentration is much higher than peak plasma levels of TMZ measured in patients (13.7 µg/ml) (Portnow et al., Clin Cancer Res 15, 7092-7098, 2009).

The results demonstrate that both taurolidine and taurultam are effective against CSCs and this finding was established for glioma CSCs from two species, mouse and man.

Figure 3:
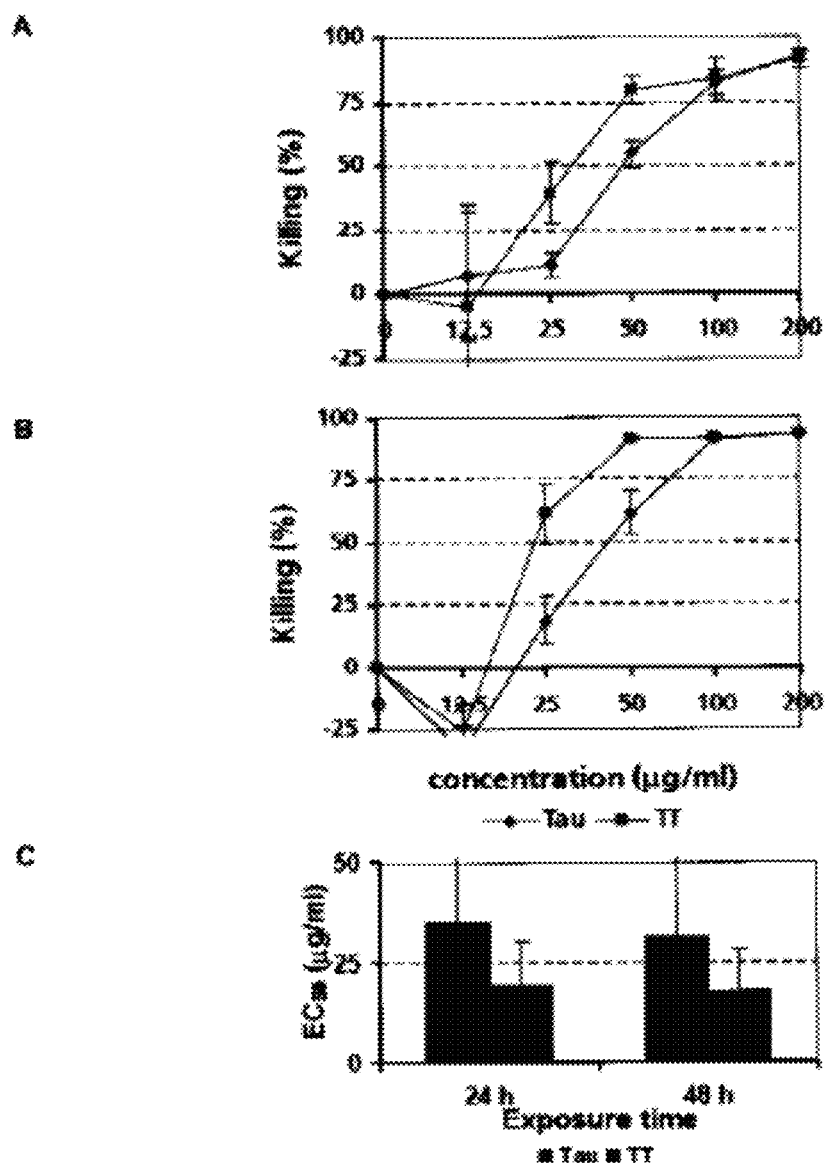
FIG. 3A-C Cytotoxicity induced in murine SMA 560 bulk glioma cells after treatment with taurolidine and taurultam (TT). Cytotoxicity was assessed after 24 h (FIG. 3A) and 48 h (FIG. 3B) of treatment. The $EC_{50}$ values for taurolidine (34.6 µg/ml) and taurultam (19.3 µg/ml) are given in the lower panel (FIG. 3C). Data are presented as mean values±SD of three independent experiments.
Figure 4:
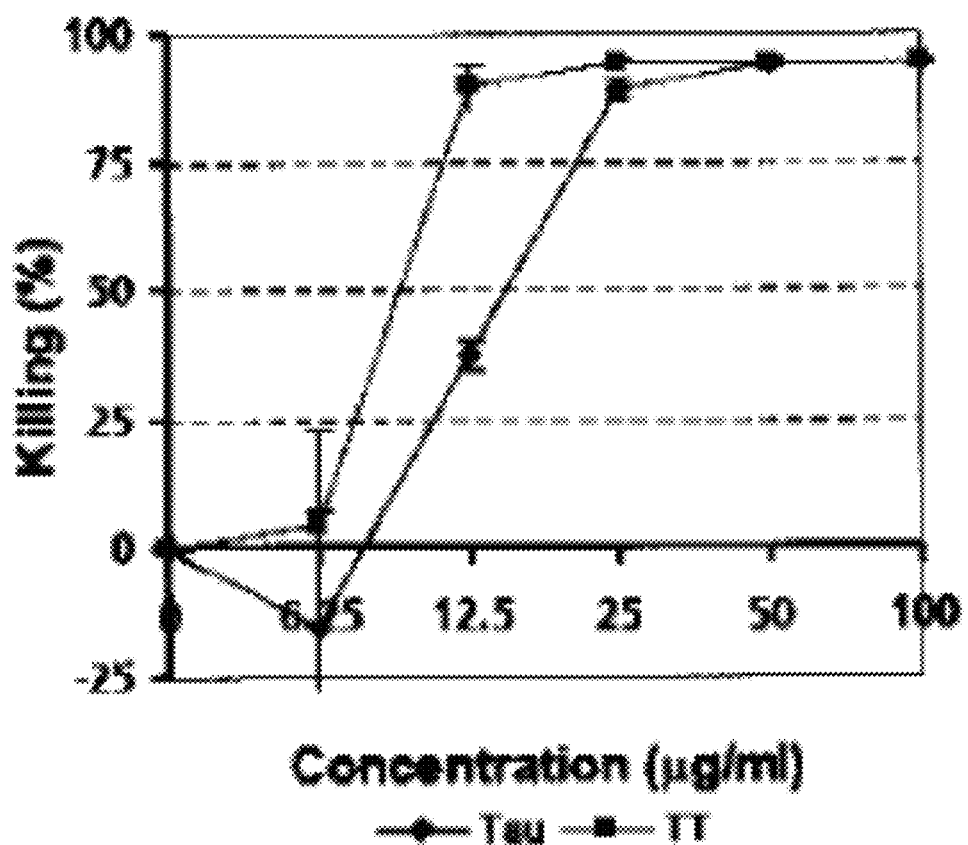
FIG. 4 Cytotoxicity induced by taurolidine and taurultam (TT) in murine SMA560 glioma cancer stem cells (CSC). Data are presented as mean values±SD.

The mouse CSCs were generated from a mouse glioma cell line (SMA 560). Remarkably, based on the $EC_{50}$ values, the CSCs were even more sensitive to taurolidine and taurultam than the corresponding glioma bulk cells (about 3 fold for taurolidine and 2 fold for taurultam) (FIGS. 3, 4).

Human CSCs, freshly isolated from four human glioblastoma patients, were likewise highly chemosensitive to both taurolidine and taurultam. The $EC_{50}$ values for cytotoxicity were 13±2 µg/ml and 11 ±1.4 µg/ml, respectively (Table 2). These values demonstrate that the human CSCs, like their murine counterparts, are more sensitive to taurolidine and taurultam (about 3 to 4 fold) than the human glioblastoma bulk cells which display $EC_{50}$ values in the range of 50 µg/ml (Rodak et al., J. Neurosurg., 102, 1055-68, 2005).

TABLE 2

Cytotoxicity Induced by taurolidine (Tau), taurultam (TT) or temozolamide (TMZ) in cancer stem cells (CSC) derived from four glioblastoma patients. $EC_{50}$ (µg/ml) = drug concentration resulting in 50% cell death compared to untreated control cultures in vitro.

| Cancer Stem Cells | n | Cytotoxicity EC50 (µg/ml) 24 h | | |
|---|---|---|---|---|
| | | Taurolidine | Taurultam | Temozolamide |
| GBM #3 | 3 | 15 | 10.5 | 84.4 (435 µM) |
| GBM #4 | 2 | 12.5 | 12.5 | 97 (500 µM) |
| GBM #5 | 2 | 14 | 11 | 48.5 (250 µM) |
| GBM #6 | 3 | 10 | 9 | 44 (230 µM) |
| Mean ± SD | | 13 ± 2 | 11 ± 1.4 | 68.5 ± 26 |

Example 8

Taurolidine and taurultam were tested against cancer stem cells derived from a murine glioma cell line and human cancer stem cells. Taurolidine and taurultam were found to exert potent anti-neoplastic activity against cancer stem cells derived from a murine glioma cell line ($EC_{50}$=12.5 µg/ml for taurolidine, $EC_{50}$=10 µg/ml for taurultam) as well as against human cancer stem cells, freshly isolated from four glioblastoma patients ($EC_{50}$=13±2 µg/ml for taurolidine; $EC_{50}$=11±1.4 µg/ml for taurultam).

The invention claimed is:

1. A compound selected from the group consisting of:

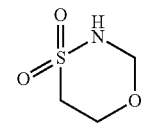

2250

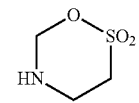

A1

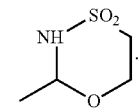

2256

2. The compound of claim 1, comprising compound 2250.

3. A method of treating cancer in a subject comprising administering to said subject a compound selected from the group consisting of:

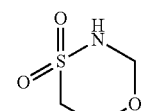

2250

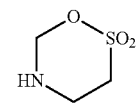

A1

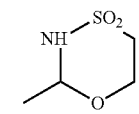

2256 wherein said cancer is glioblastoma, glioma, neuroblastoma, astrocytoma, carcinomatous meningitis, colon cancer, rectal cancer, colo-rectal cancer, ovarian cancer, breast cancer, prostate cancer, lung cancer, mesothelioma, melanoma, renal cancer, liver cancer, pancreatic cancer, gastric cancer, esophageal cancer, urinary bladder cancer, cervical cancer, cardiac cancer, gall bladder cancer, skin cancer, bone cancer, cancers of the head or neck, leukemia, lymphoma, lymphosarcoma, adenocarcinoma, or fibrosarcoma, or metastases thereof.

4. The method of claim 3, wherein cancer cells of said cancer are killed, or growth of said cancer cells is inhibited, by at least one of oxidative stress, apoptosis, anti-angiogenesis or antitubulogenesis.

5. The method of claim 3, wherein said compound is 2250.

6. A method of treating glioblastoma in a subject, comprising administering to said subject the compound of claim 2.

7. A method of treating glioma in a subject, comprising administering to said subject the compound of claim 2.

8. A method of treating bacterial infection in a subject comprising administering to said subject a compound selected from the group consisting of:

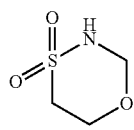

2250

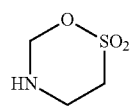

A1

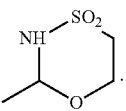

2256

9. The method of claim 8 wherein said compound is 2250.

10. The method of claim 8 wherein said bacterial infection is *S. aureaus, E. coli, H. pylori* or MRSA infection.

11. A method of treating tumor stem cells in a subject comprising administering to said subject a compound selected from the group consisting of:

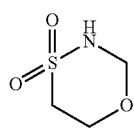

2250

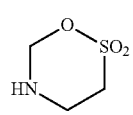

A1

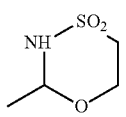

2256 wherein said tumor stem cells are in a subject suffering from glioblastoma, glioma, neuroblastoma, astrocytoma, carcinomatous meningitis, colon cancer, rectal cancer, colo-rectal cancer, ovarian cancer, breast cancer, prostate cancer, lung cancer, mesothelioma, melanoma, renal cancer, liver cancer, pancreatic cancer, gastric cancer, esophageal cancer, urinary bladder cancer, cervical cancer, cardiac cancer, gall bladder cancer, skin cancer, bone cancer, cancers of the head or neck, leukemia, lymphoma, lymphosarcoma, adenocarcinoma, or fibrosarcoma, or metastases thereof.

12. The method of claim 11 wherein said compound is 2250.

13. A method of treating glioblastoma tumor stem cells in a subject comprising administering to said subject a compound selected from the group consisting of:

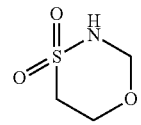

2250

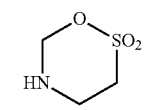

A1

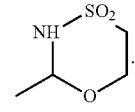

2256

14. The method of claim 13 wherein said compound is 2250.

15. A method of killing tumor stem cells comprising administering to a subject in need thereof a compound selected from the group consisting of

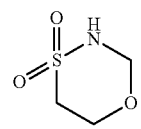

2250

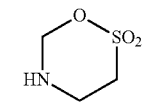

A1

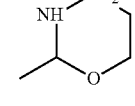

2256

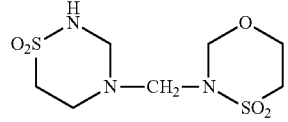

B1 in combination with taurolidine and/or taurultam.

* * * * *